(12) United States Patent
Weiner et al.

(10) Patent No.: US 8,926,648 B2
(45) Date of Patent: Jan. 6, 2015

(54) MULTI-METHOD AND MULTI-APPARATUS FOR TREATING OBESITY

(76) Inventors: Brian Charles Weiner, Morganville, NJ (US); Sarah Hedy Weiner, Morganville, NJ (US)

(*) Notice: Subject to any disclaimer, the term of this patent is extended or adjusted under 35 U.S.C. 154(b) by 1435 days.

(21) Appl. No.: 12/069,681

(22) Filed: Feb. 12, 2008

(65) Prior Publication Data

US 2008/0208241 A1    Aug. 28, 2008

Related U.S. Application Data

(60) Provisional application No. 60/901,044, filed on Feb. 13, 2007.

(51) Int. Cl.
*A61M 29/00* (2006.01)
*A61F 5/00* (2006.01)

(52) U.S. Cl.
CPC ............... *A61F 5/003* (2013.01); *A61F 5/0036* (2013.01)
USPC ....................................................... 606/192

(58) Field of Classification Search
USPC ............... 606/192, 153, 108, 191; 604/96.01, 604/103.03, 264; 623/23.67
See application file for complete search history.

(56) References Cited

U.S. PATENT DOCUMENTS

| | | | |
|---|---|---|---|
| 766,336 A | 8/1904 | Farrington | |
| 797,676 A | 8/1905 | Flowers | |
| 4,416,267 A | 11/1983 | Garren | |
| 4,648,383 A * | 3/1987 | Angelchik | 128/899 |
| 4,694,827 A | 9/1987 | Weiner | |
| 6,245,040 B1 * | 6/2001 | Inderbitzen et al. | 604/103.07 |
| 7,033,384 B2 * | 4/2006 | Gannoe et al. | 623/1.11 |
| 2005/0049677 A1 * | 3/2005 | Farnan | 623/1.15 |
| 2005/0267596 A1 * | 12/2005 | Chen et al. | 623/23.67 |
| 2006/0271088 A1 * | 11/2006 | Alfrhan | 606/192 |
| 2006/0282107 A1 * | 12/2006 | Hashiba et al. | 606/153 |
| 2007/0016262 A1 * | 1/2007 | Gross et al. | 607/40 |
| 2007/0100368 A1 * | 5/2007 | Quijano et al. | 606/192 |
| 2007/0100369 A1 * | 5/2007 | Cragg et al. | 606/192 |
| 2007/0156248 A1 * | 7/2007 | Marco et al. | 623/23.7 |
| 2008/0234718 A1 * | 9/2008 | Paganon et al. | 606/192 |

* cited by examiner

*Primary Examiner* — Thomas McEvoy
*Assistant Examiner* — Julie A Szpira
(74) *Attorney, Agent, or Firm* — Jon Fallon, Esq.; Michael P. Kochka, Esq.

(57) ABSTRACT

A multi-method and multi-apparatus for treating obesity. The multi-method includes a method for estimating a volume of an intragastric balloon appropriate for an individual patient, a method for using an enterocutaneous fistula to inspect an intragastric balloon without sedation and endoscopic complications associated with an upper endoscopy, and a method for decreasing ability of the stomach of an individual patient to distend or expand after a meal increasing satiety and helping the individual patient to comply with a weight loss diet. The multi-apparatus includes an intragastric balloon for inflating without installation of a pressurized gas or liquid, an intragastric balloon for minimizing trauma of the intragastric balloon on the gastric mucosa, and an intragastric balloon for administering therapeutic medications.

17 Claims, 18 Drawing Sheets

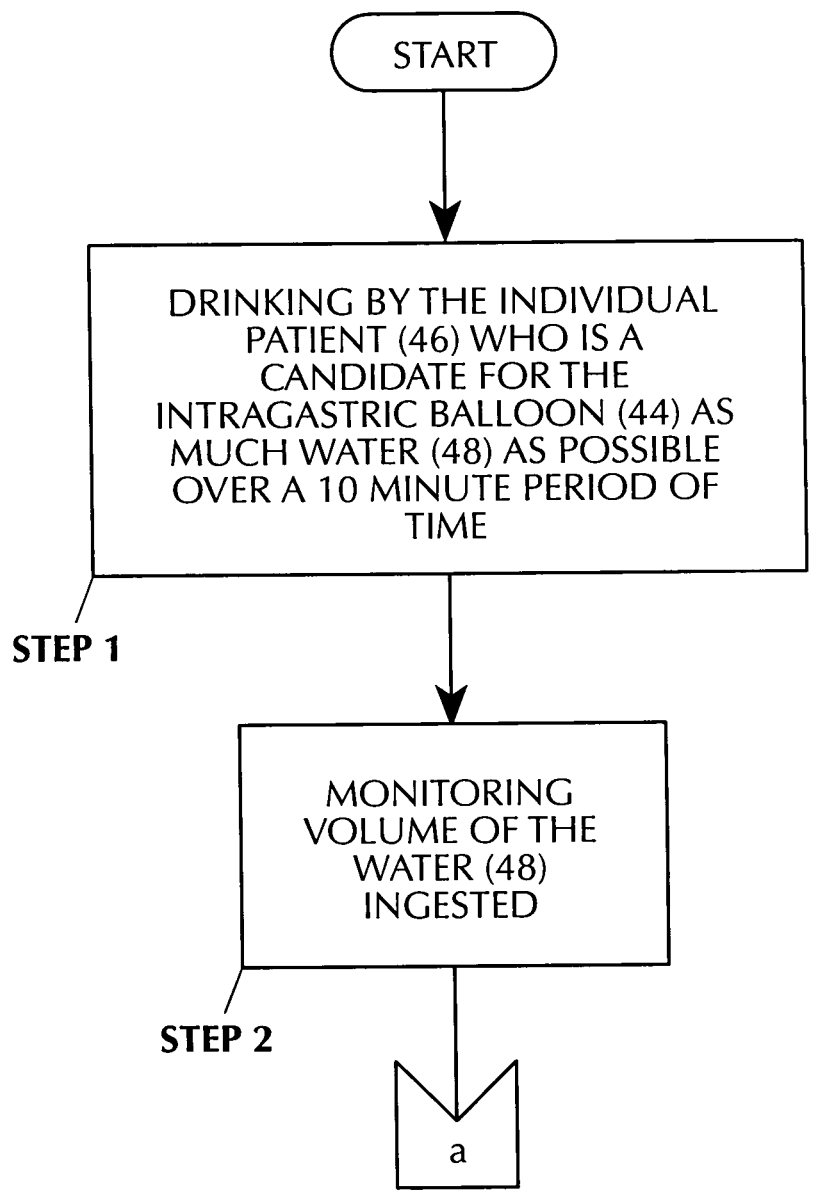
FIG. 2-A

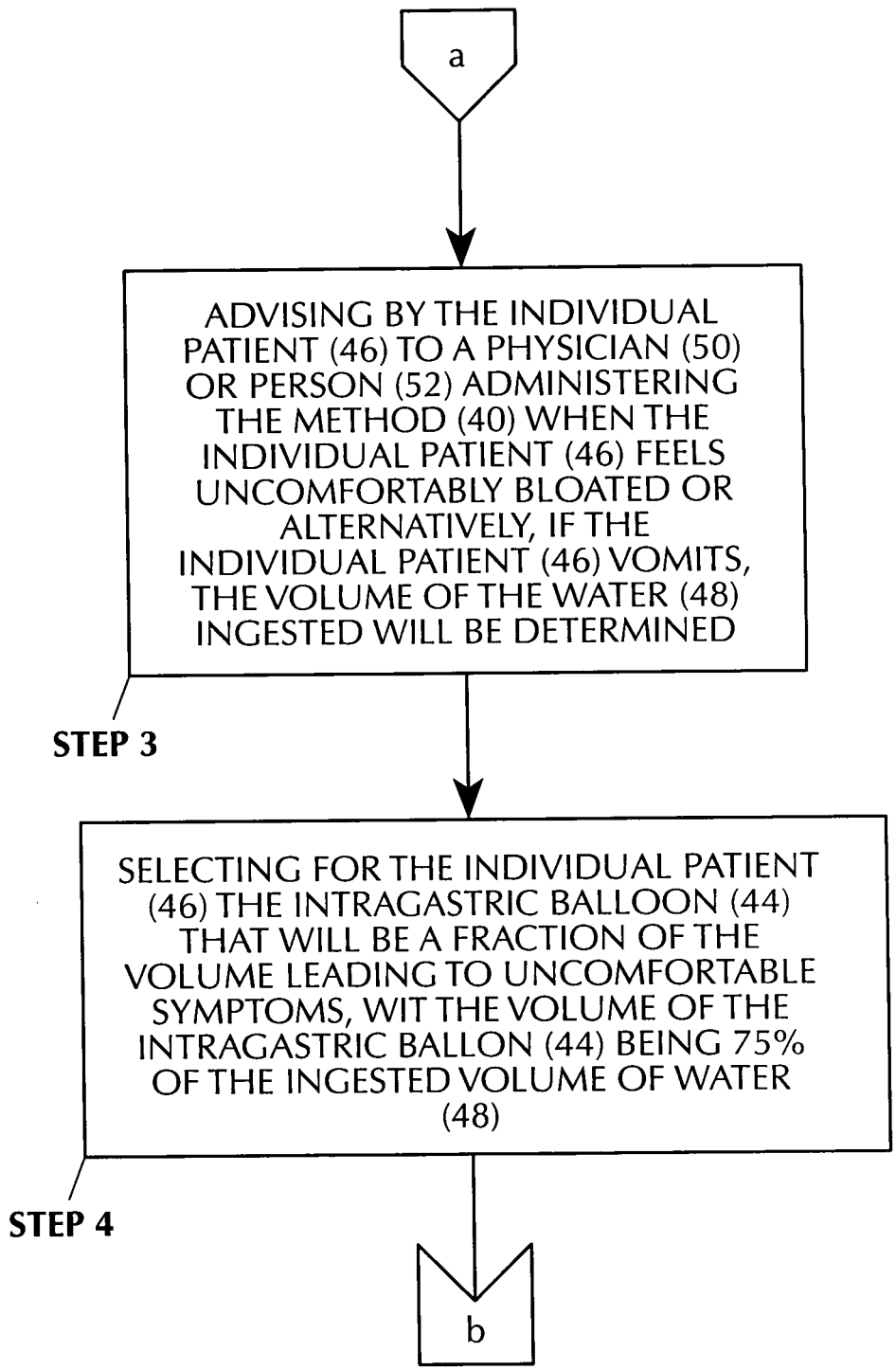
FIG. 2-B

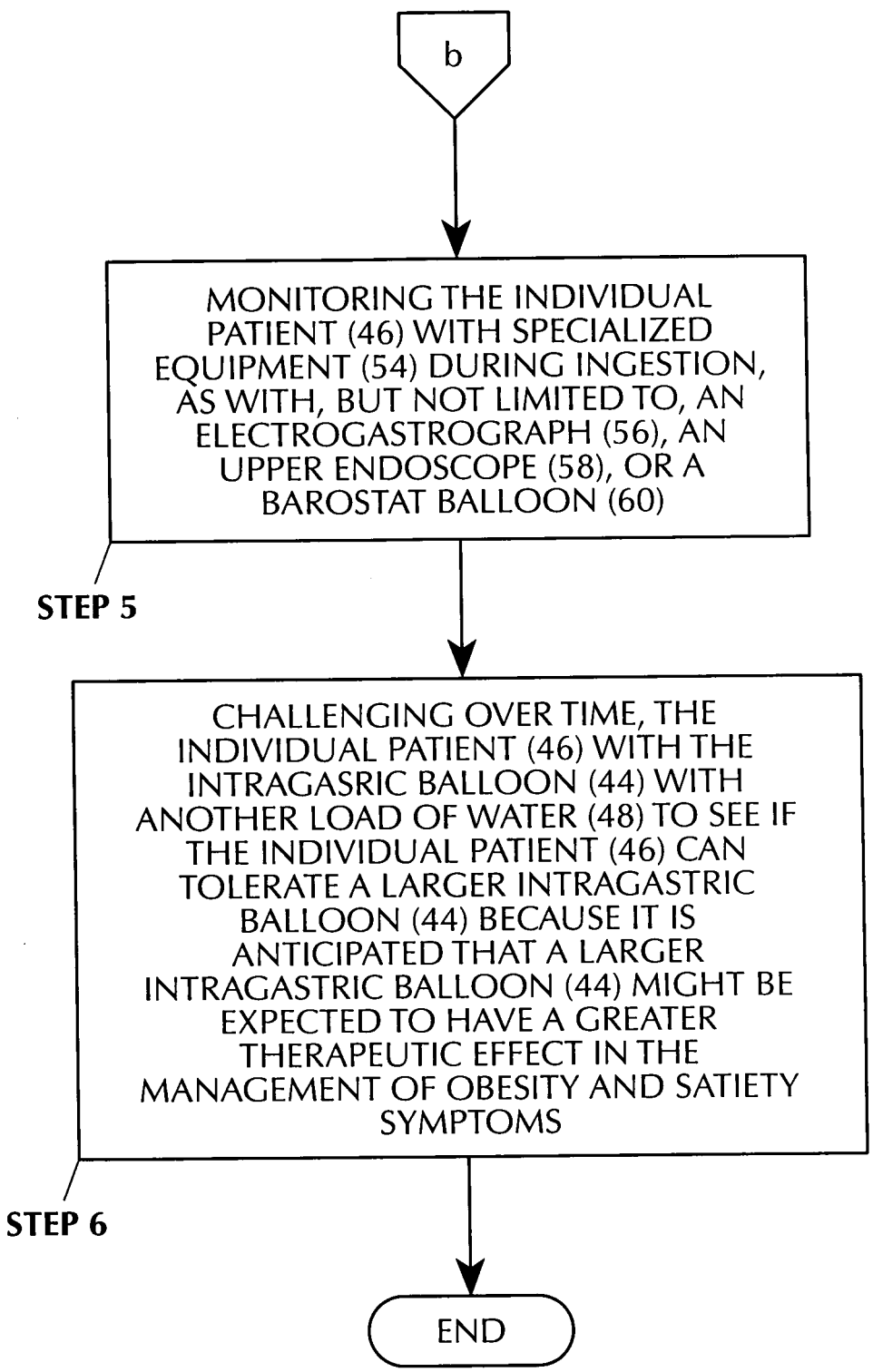
FIG. 2-C

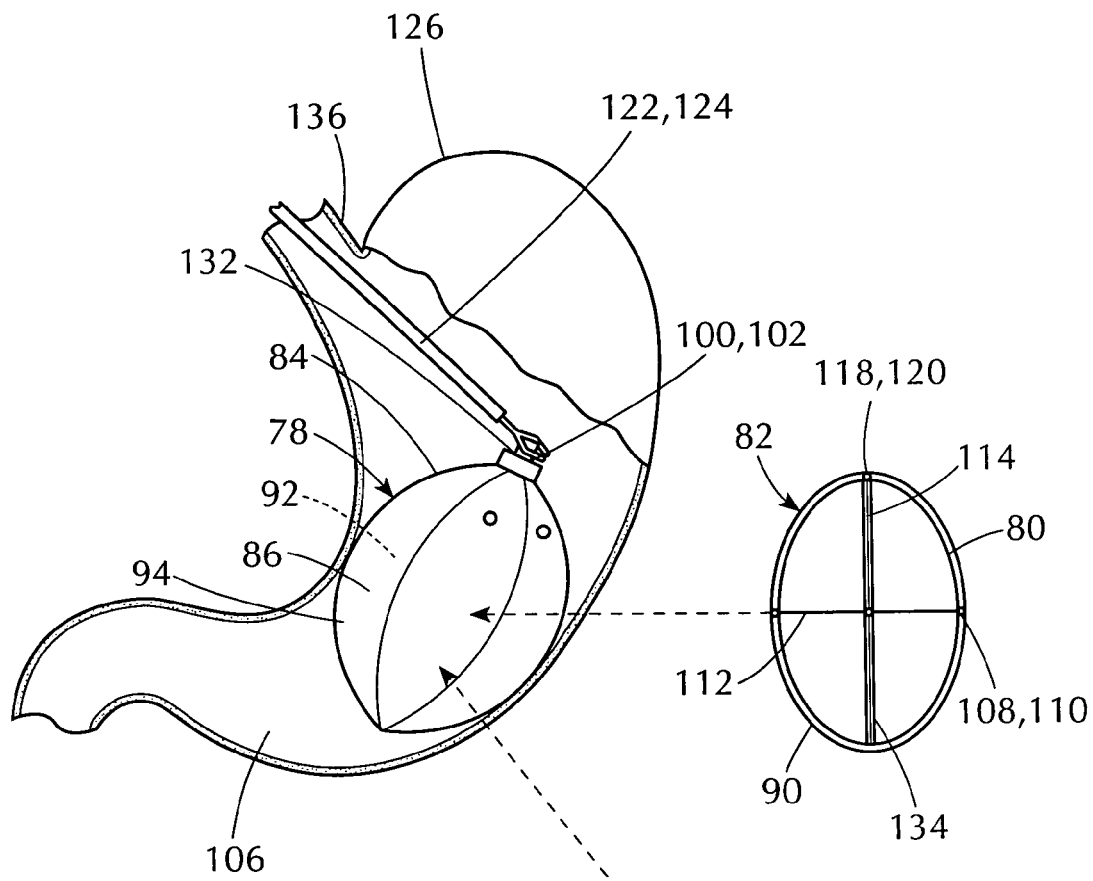
FIG. 3
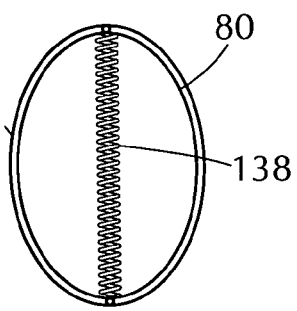

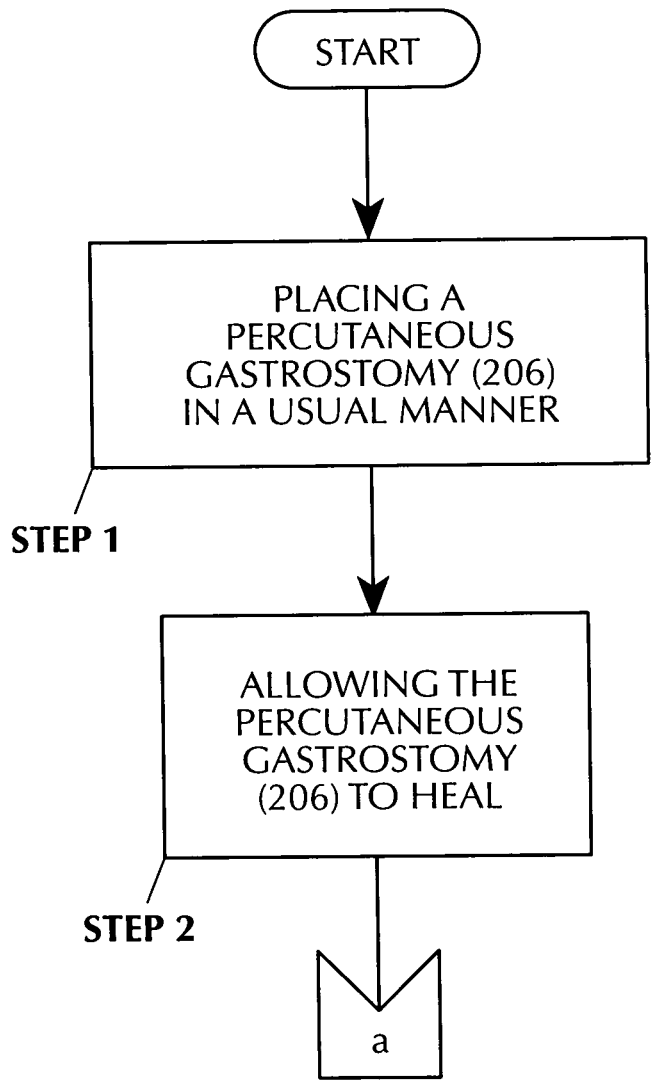
FIG. 10-A

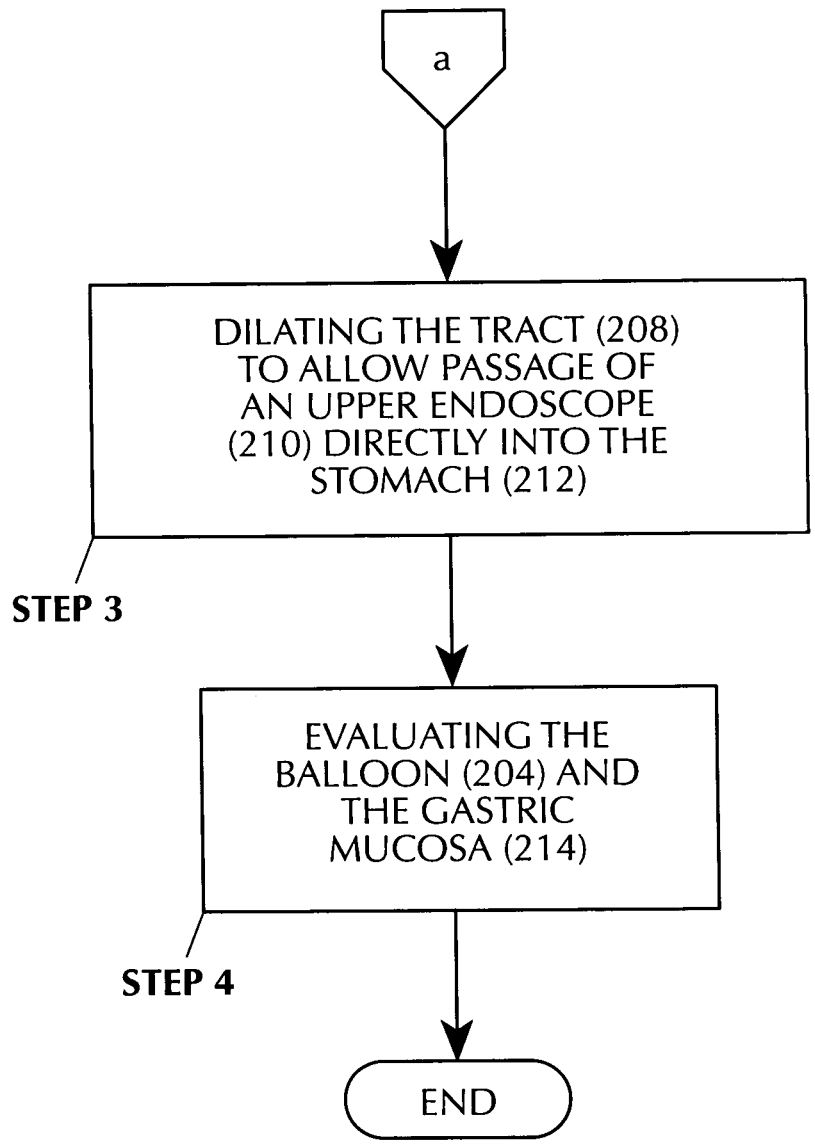
FIG. 10-B

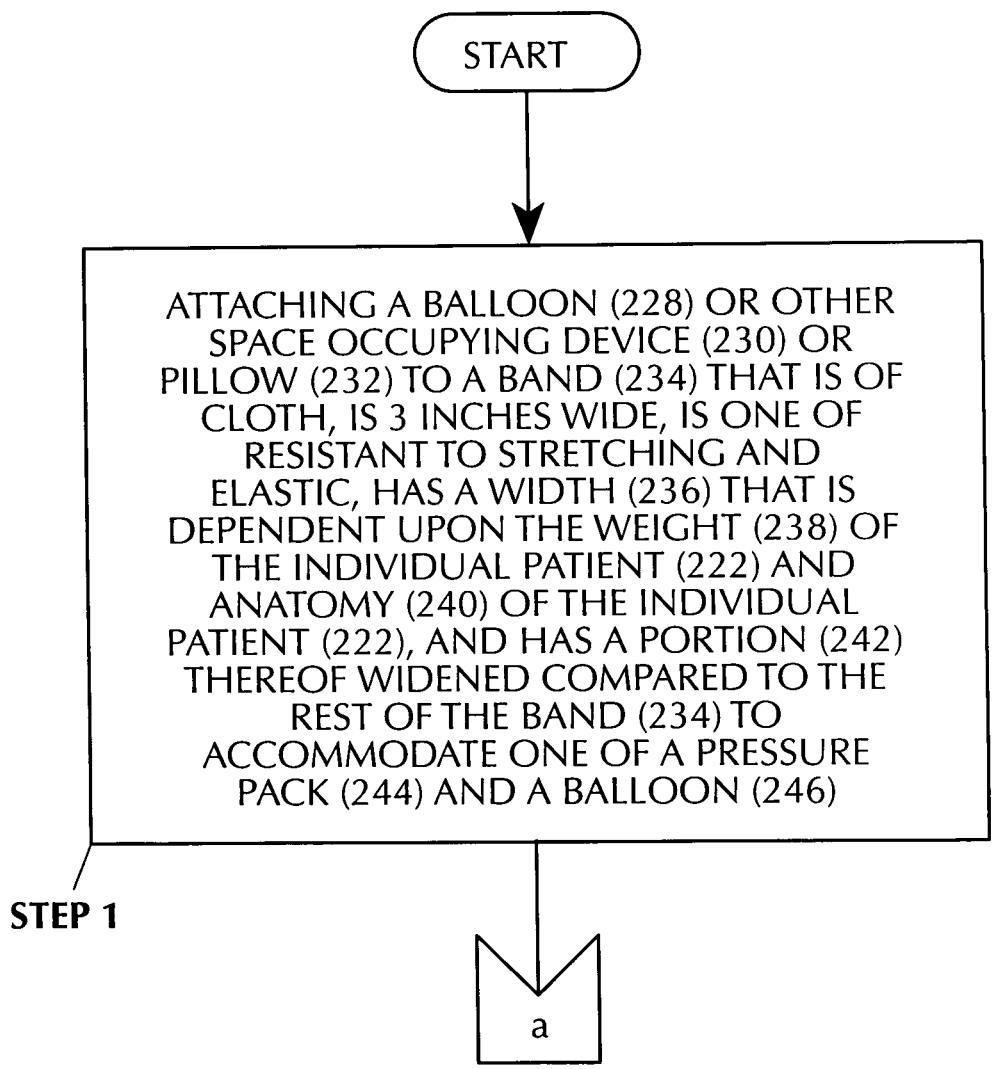
FIG. 11-A

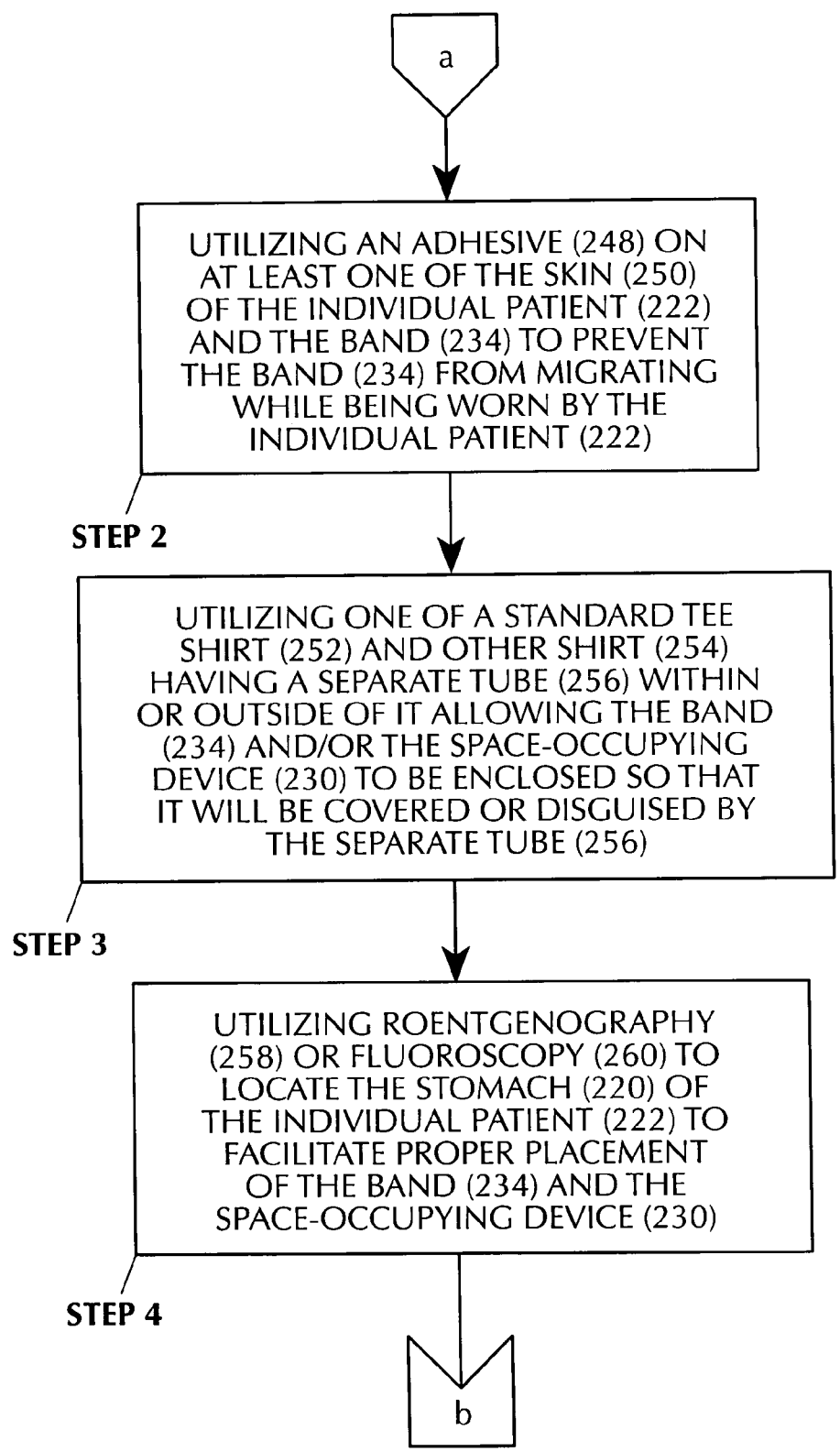
FIG. 11-B

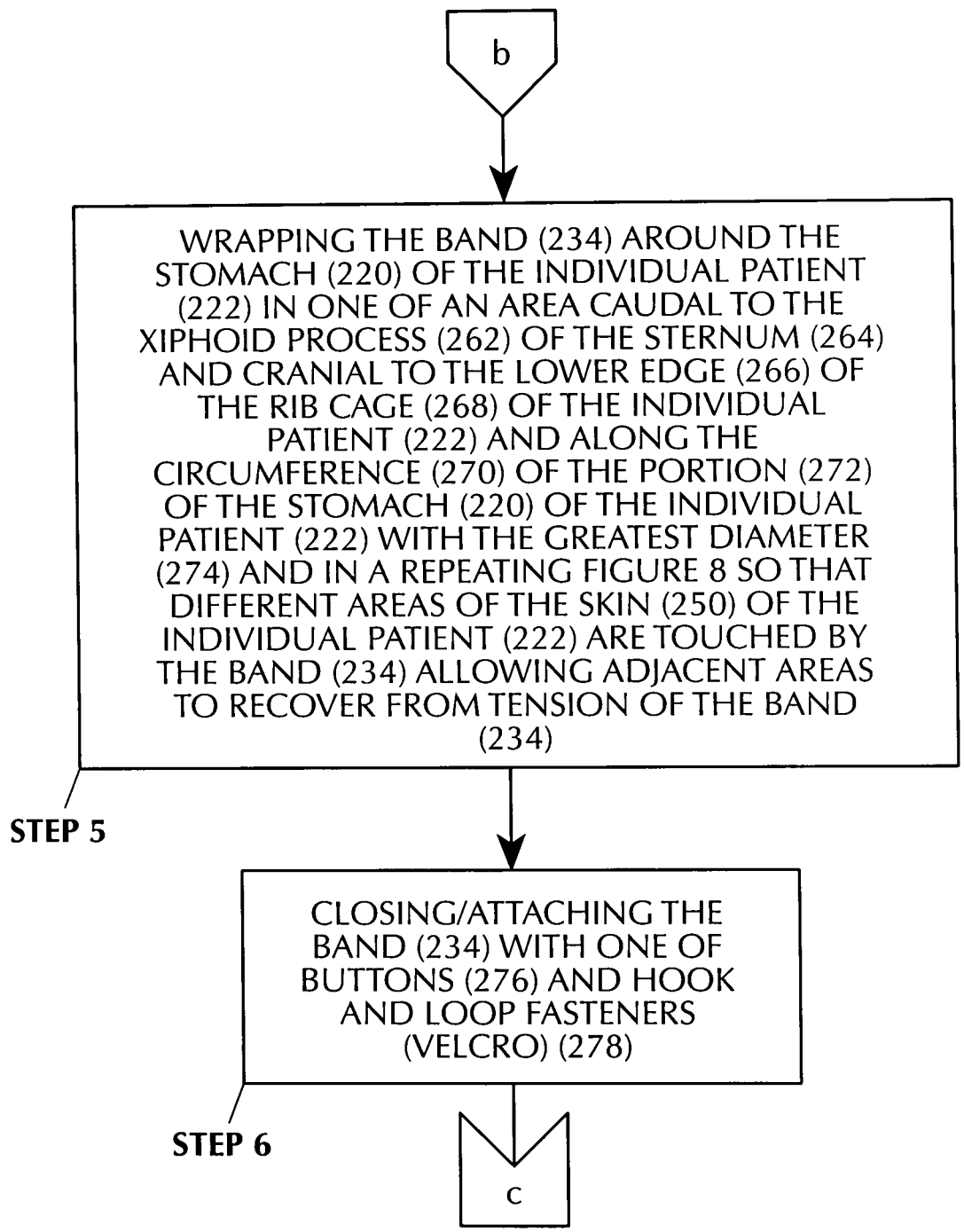
FIG. 11-C

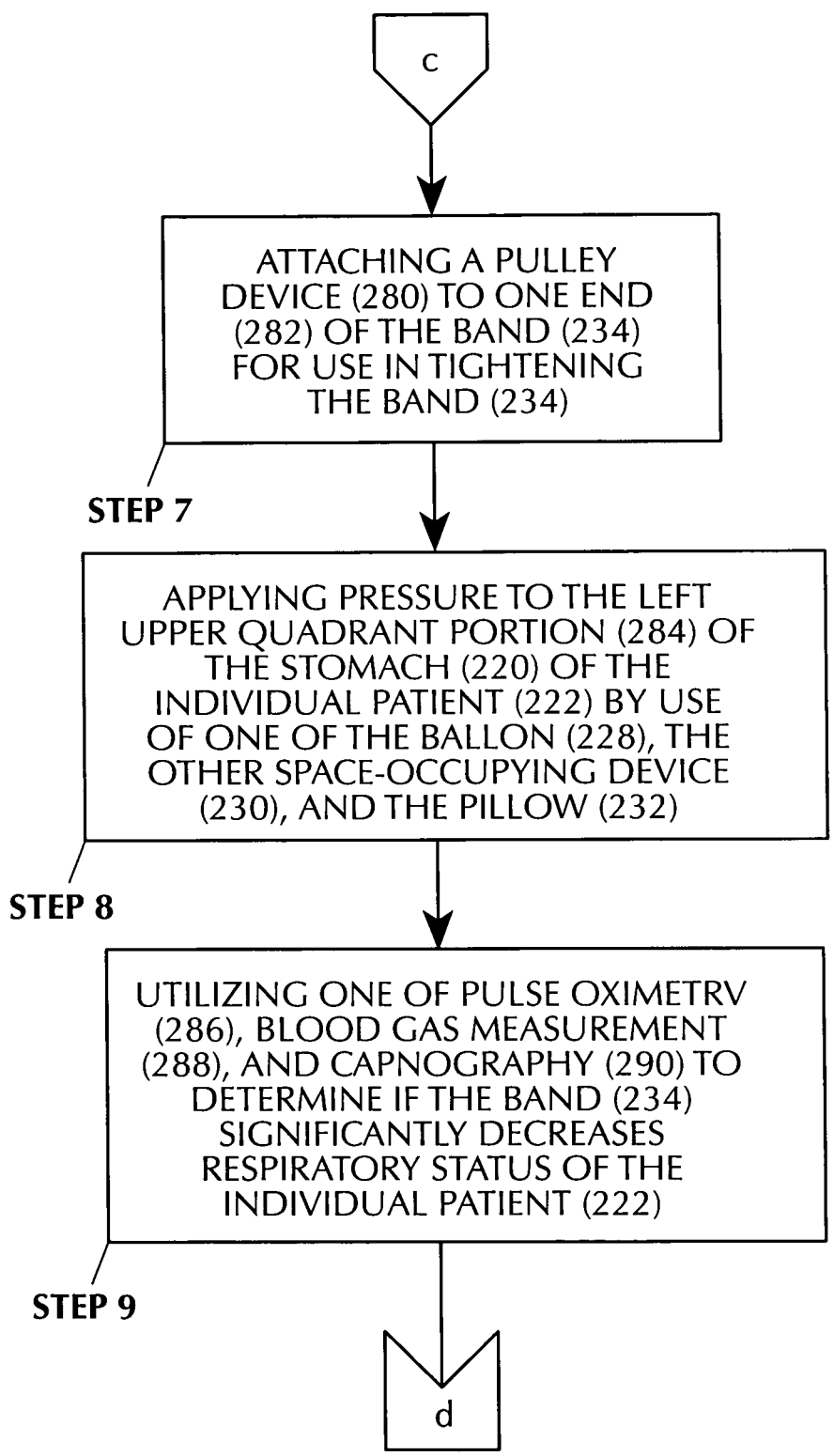
FIG. 11-D

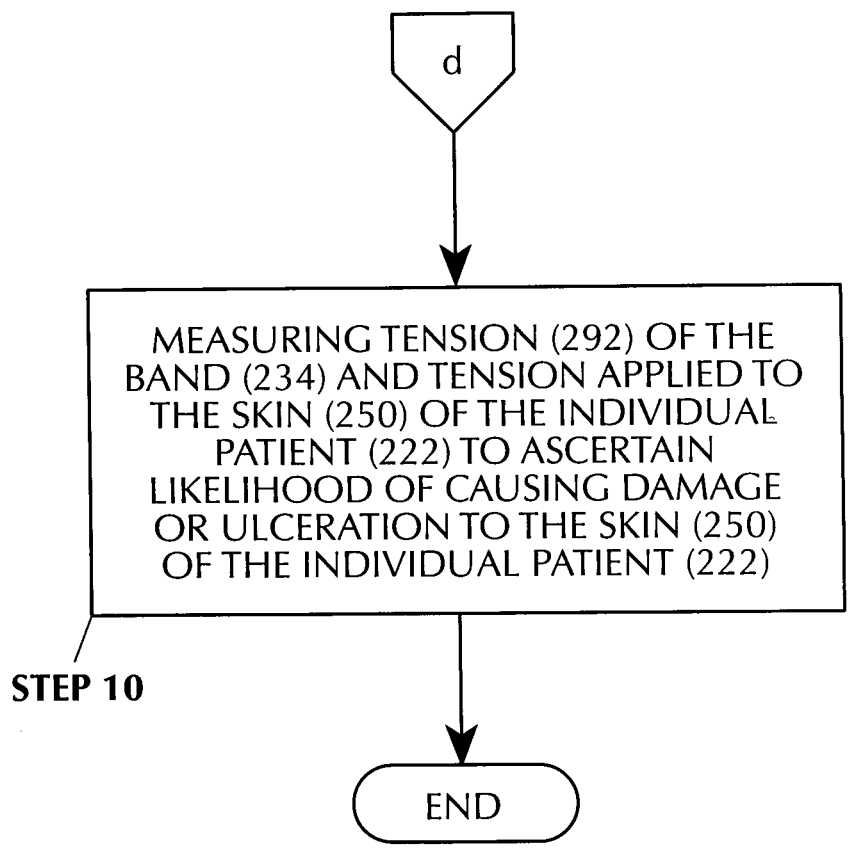
FIG. 11-E

MULTI-METHOD AND MULTI-APPARATUS FOR TREATING OBESITY

1. CROSS REFERENCE TO RELATED APPLICATIONS

The instant non-provisional patent application claims priority from provisional patent application No. 60/901,044, filed on Feb. 13, 2007, for METHODS FOR TREATMENT OF OBESITY, and incorporated herein by reference thereto.

2. BACKGROUND OF THE INVENTION

A. Field of the Invention

The embodiments of the present invention relate to a treatment for obesity, and more particularly, the embodiments of the present invention relate to a multi-method and multi-apparatus for treating obesity.

B. Description of the Prior Art

In the published medical literature, there are a significant number of patients who experience adverse gastrointestinal complaints in the period immediately after the deployment of an intragastric balloon. In this experience, all patients are treated with one specific model and size of balloon.

Thus, there exists a need for an intragastric balloon wherein both the geometry or shape of the balloon, as well as the volume of the balloon, are components that can be manipulated to enhance the therapeutic effect and to minimize complications.

In the published medical literature, intragastric balloons are placed in a deflated form and than inflated once in the stomach. The only material holding the balloons in their active shape is either air, liquid, or both. It is possible for these substances to leak out of the balloon causing the balloon to deflate and fail.

Thus, there exists a need for an intragastric balloons including a skeleton of metal struts that strengthen the balloon structure and prevent premature balloon failure, which could lead to a loss of therapeutic effect in obesity and can also lead to small bowel obstruction or gastric outlet obstruction.

In the published medical literature, intragastric balloons have been associated with the complication of irritation of the lining of the stomach (gastritis) and gastric ulceration. Considering the example of the intragastric balloon already patented by the instant inventors as U.S. Pat. No. 4,694,827, this complication was contemplated and a solution offered by using an intragastric balloon having protrusions and channels.

Non-compliance with therapeutic medications is a well known clinical problem interfering with good patient outcomes. Many different solutions have been attempted to deal with this problem, and to date, none have been completely satisfactory.

In the medical literature, damage to the lining of the stomach has been a major complication of intragastric balloon therapy. In many cases, severe damage, such as ulceration, may require removal of the balloon. Alternatively, there are many cases of patients with symptoms that might be related to the intragastric balloon, but might also be related to intercurrent viral illnesses, food poisoning, or milder complications of balloon therapy, not necessitating balloon extraction. In current practice, patients would undergo an upper endoscopy to assess the situation.

There are a multitude of methods purported to treat obesity in humans. Among the most effective of these methods are surgical techniques that alter the volume of the stomach available to receive food from the mouth and esophagus. The most popular of these surgical techniques is often referred to as a (Roux en Y) gastric bypass procedure. The gastric bypass is thought to work by limiting the amount of food that can be ingested at one time, although it may also alter gastrointestinal hormones and decrease the appetite.

Numerous innovations for inflatable medical devices have been provided in the prior art, which will be described below in chronological order to show advancement in the art, and which is incorporated herein by reference thereto. Even though these innovations may be suitable for the specific individual purposes to which they address, however, they differ from the present invention in that they do not teach a multi-method and multi-apparatus for treating obesity.

(1) U.S. Pat. No. 766,336 to Farrington.

U.S. Pat. No. 766,336 issued to Farrington on Aug. 2, 1904 teaches a device including a fluid-supply tube having a plurality of parallel slots and springs arranged within the tube and adapted to be partly projected through the slots. The springs have their inner ends secured to the tube. An adjustable member is secured to the outer ends of the springs. Elastic covers extend around that portion of the springs projecting through the slots.

(2) U.S. Pat. No. 797,676 to Flowers.

U.S. Pat. No. 797,676 issued to Flowers on Aug. 22, 1905 teaches a syringe including a nozzle having outlets and an expandable sack enveloping the nozzle, having outlets, and formed with longitudinal ribs stiffening and reinforcing the sack in the direction of its length and admitting of its diametrical expansion.

(3) U.S. Pat. No. 4,416,267 to Garren et al.

U.S. Pat. No. 4,416,267 issued to Garren et al. on Nov. 22, 1983 in class 128 and subclass 1 R teaches a stomach insert for treating obesity in humans by reducing the stomach volume, which includes a flexible torus-shaped inflatable balloon having a central opening extending therethrough. At least a portion of the balloon has a self-sealing substance to facilitate puncture thereof with a needle for inflating the balloon and sealing of the puncture upon removal of the needle. The method includes positioning the balloon inside the stomach of the person being treated for obesity so as to reduce the stomach volume.

(4) U.S. Pat. No. 4,694,827 to Weiner et al.

U.S. Pat. No. 4,694,827 issued to Weiner et al. on Sep. 22, 1987 in class 128 and subclass 303 R teaches generally, a balloon insertable and inflatable in the stomach to deter ingestion of food and having, when inflated, a plurality of smooth-surfaced convex protrusions disposed to permit engagement of the stomach wall by the balloon only at spaced localities for minimizing mechanical trauma of the stomach wall by the balloon.

Specifically, as shown in FIG. 1, which is a diagrammatic side elevational view in partial section of a prior art balloon fully expanded within a stomach, a balloon 10 being flexible-walled, imperforate, air-inflatable, and insertable and inflatable within the stomach 12 of a human 14 or animal 16 to deter ingestion of food 18 by occupying a substantial portion 20 of the volume 22 of the stomach 12 is taught. The balloon 10 has a plurality of wall portions 24 forming protrusions 26 that are smooth-surfaced, convex, and outward when inflated. The protrusions 26 are distributed around the balloon 10 and cooperatively define a plurality of channels 28 that are outwardly open for passage of fluent material 30 between the outer surface 32 of the balloon 10 and the wall 34 of the stomach 12, and are shaped and disposed to permit engagement of the wall 34 of the stomach 12 by the balloon 10 only at spaced localities 36 so as to maintain a substantial portion 38 of the wall 34 of the stomach 12 away from contact with the balloon 10 for minimizing complications due to mechanical trauma of the balloon 10 against the wall 34 of the stomach 12.

The protrusions 26 and the channels 28 minimize physical contact with the wall 34 of the stomach 12 and stimulate cytoprotection. Cytoprotection is an innate mechanism of preservation of the stomach 12 from adverse effects of a harsh environment of a gastric lumen.

It is apparent that numerous innovations for inflatable medical devices have been provided in the prior art that are adapted to be used. Furthermore, even though these innovations may be suitable for the specific individual purposes to which they address, however, they would not be suitable for the purposes of the embodiments of the present invention as heretofore described, namely, a multi-method and multi-apparatus for treating obesity.

3. SUMMARY OF THE INVENTION

Thus, an object of the embodiments of the present invention is to provide a multi-method and multi-apparatus for treating obesity, which avoids the disadvantages of the prior art.

Briefly stated, another object of the embodiments of the present invention is to provide a multi-method and multi-apparatus for treating obesity. The multi-method includes a method for estimating a volume of an intragastric balloon appropriate for an individual patient, a method for using an enterocutaneous fistula to inspect an intragastric balloon without sedation and endoscopic complications associated with an upper endoscopy, and a method for decreasing ability of the stomach of an individual patient to distend or expand after a meal to increase satiety and help the individual patient to comply with a weight less diet. The multi-apparatus includes an intragastric balloon for inflating without installation of a pressurized gas or liquid, an intragastric balloon for minimizing trauma of the intragastric balloon on the gastric mucosa, and an intragastric balloon for administering therapeutic medications.

The novel features considered characteristic of the embodiments of the present invention are set forth in the appended claims. The embodiments of the present invention themselves, however, both as to their construction and their method of operation together with additional objects and advantages thereof will be best understood from the following description of the specific embodiments when read and understood in connection with the accompanying drawing.

4. BRIEF DESCRIPTION OF THE DRAWING

The figures of the drawing are briefly described as follows:

FIGS. 2A-2C are a flowchart of the method of an embodiment of the present invention for estimating volume of an intragastric balloon appropriate for an individual patient;

FIG. 3 is a diagrammatic side elevational view in partial section of a balloon of an embodiment of the present invention fully expanded within a stomach;

Figure 1:
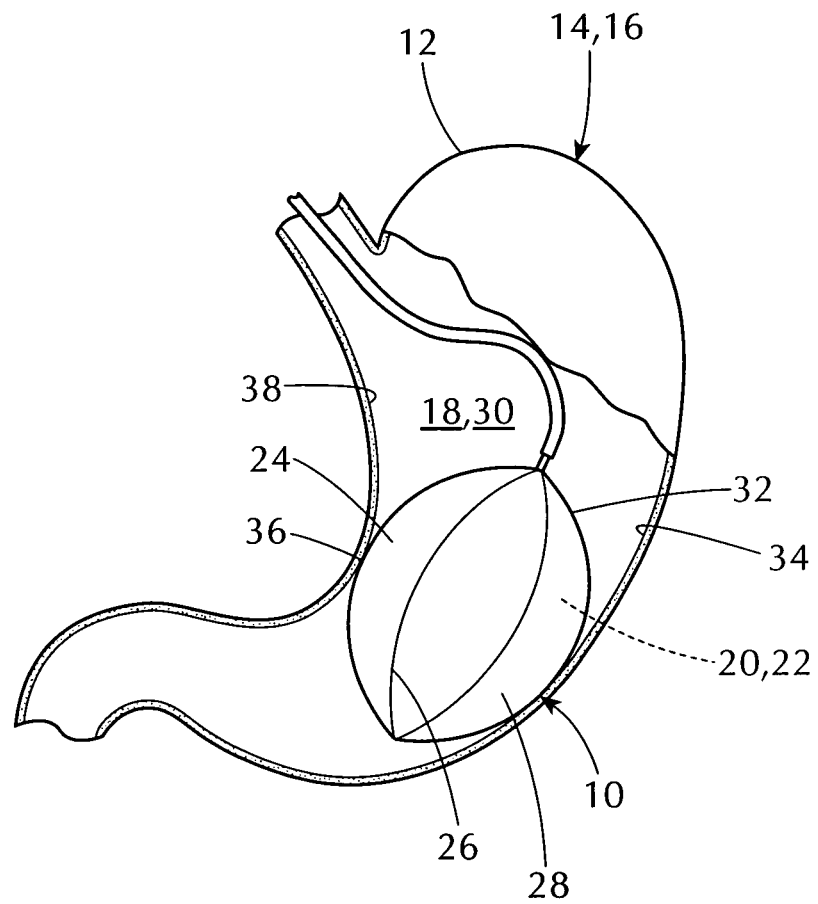
FIG. 1 is a diagrammatic side elevational view in partial section of a prior art balloon fully expanded within a stomach.

FIG. 10A-10B are a flowchart of the method of another embodiment of the present invention for using an enterocutaneous fistula to inspect an intragastric balloon without sedation and endoscopic complications associated with an upper endoscopy; and FIGS. 11A-11E are a flowchart of the method of another embodiment of the present invention for decreasing ability of the stomach of an individual patient to distend or expand after a meal increasing satiety and helping the individual patient to comply with a weight loss diet.

5. LIST OF REFERENCE NUMERALS UTILIZED IN THE DRAWING

A. Prior Art 10 balloon
12 stomach of human 14 or animal 16
14 human
16 animal
18 food
20 substantial portion of volume 22 of stomach 12
22 volume of stomach 12
24 plurality of wall portions
26 protrusions
28 plurality of channels
30 fluent material
32 outer surface of balloon 10
34 wall of stomach 12
36 spaced localities
38 substantial portion of wall 34 of stomach 12

B. Method of Embodiment of Present Invention for Estimating Volume of Intragastric Balloon Appropriate for Individual Patient 40 method of embodiment of present invention for estimating volume 42 of intragastric balloon 44 appropriate for individual patient 46
42 volume of intragastric balloon 44 appropriate for individual patient 46
44 intragastric balloon appropriate for individual patient 46
46 individual patient
48 water of material 62 ingested
50 physician administering method 40
52 person administering method 40
54 specialized equipment
56 electrogastrograph of specialized equipment 54
58 upper endoscope of specialized equipment 54
60 barostat balloon of specialized equipment 54
62 material ingested
64 water solution suspension of material 62 ingested
66 non-aqueous based material of material 62 ingested
68 temperature
70 room temperature of temperature 68

72 other temperature of temperature 68
74 10 minutes time
76 other interval of time

C. Intragastric Balloon for Inflating without Installation of Pressurized Gas or Liquid 78 intragastric balloon
80 plurality of struts
82 skeleton of intragastric balloon 78
84 protrusions of intragastric balloon 78
86 channels of intragastric balloon 78
90 shape
92 volume of intragastric balloon 78
100 valve of intragastric balloon 78
102 opening of intragastric balloon 78
106 gastric environment
108 holes of plurality of struts 80
110 fastening points of plurality of struts 80
112 internal wires
114 central longitudinal strut of plurality of struts 80
118 one end of central longitudinal strut 114 of plurality of struts 80
120 portion of central longitudinal strut 114 of plurality of struts 80
122 endoscopic device
124 endoscopic forceps
126 stomach
132 grasping point
134 two parallel layers of metals of plurality of struts 80
136 esophagus
138 spring

D. Intragastric Balloon for Minimizing Trauma of Intragastric Balloon on Gastric Mucosa 140 plurality of protrusions
142 balloon
144 one of plurality of protrusions 140
145 opposite side of balloon 142
146 another one of plurality of protrusions 140
148 antral wall of stomach 152
150 proximal portion of stomach 152
152 stomach
154 distal antrum of stomach 152
156 one tether
158 long axis of central longitudinal strut 160 of plurality of struts 162
160 central longitudinal strut 160 of plurality of struts 162
162 plurality of struts
164 ball and socket assembly
168 electrical device
169 electrical signals of electrical device 168
170 antrum of stomach 152
172 counterweight
174 fixed counterweight of counterweight 172
176 plurality of struts of balloon 142

E. Intragastric Balloon for Administering Therapeutic Medications 178 therapeutic medication
180 matrix of therapeutic medication 178
182 balloon
184 one of struts 186 of balloon 182
186 struts of balloon 182
190 pocket
192 attachment in wall 194 of balloon 188
196 holes of balloon 182
198 gastric contents

F. Method for Using Enterocutaneous Fistula to Inspect Intragastric Balloon without Sedation and Endoscopic Complications Associated with Upper Endoscopy 200 method of embodiment of present invention for using enterocutaneous fistula 202 to inspect intragastric balloon 204 without sedation and endoscopic complications associated with upper endoscopy
202 enterocutaneous fistula
204 intragastric balloon
206 percutaneous gastrostomy
208 tract
210 upper endoscope
212 stomach
214 gastric mucosa

G. Method for Restricting Expansion of Stomach for Individual Patient 218 method of embodiment of present invention for decreasing ability of stomach 220 of individual patient 222 to distend or expand after meal 224 increasing satiety and helping individual patient 222 to comply with weight loss diet 226
220 stomach of individual patient 222
222 individual patient
224 meal
226 weight less diet
228 balloon
230 other space occupying device
232 pillow
234 band
236 width of band 234
238 weight of individual patient 222
240 anatomy of individual patient 222
242 portion of band 234
244 pressure pack
246 balloon
248 adhesive
250 skin of individual patient 222
252 standard tee shirt
254 other shirt
256 separate tube
258 roentgenography
260 fluoroscopy
262 xiphoid process of sternum 264 of individual patient 222
264 sternum of individual patient 222
266 lower edge of rib cage 268 of individual patient 222
268 rib cage of individual patient 222
270 circumference of portion 272 of stomach 220 of individual patient 222
272 portion of stomach 220 of individual patient 222
274 greatest diameter
276 buttons
278 hook and loop fasteners (VELCRO®)
280 pulley device
282 one end of band 234
284 left upper quadrant portion of stomach 220 of individual patient 222
286 pulse oximetry
288 blood gas measurement
290 capnography
292 tension of band 234

6. DETAILED DESCRIPTION OF THE PREFERRED EMBODIMENTS

A. A Method for Estimating Volume of an Intragastric Balloon Appropriate for an Individual Patient Referring now to the figures, in which like numerals indicate like parts, and particularly to FIGS. 2A-2C, which are a flowchart of the method of an embodiment of the present invention for estimating volume of an intragastric balloon appropriate for an individual patient, the method of an embodiment of the present invention is shown generally at 40 for estimating volume 42 of an intragastric balloon 44 appropriate for an individual patient 46, and comprises the steps of:

STEP 1: Drinking by the individual patient 46 who is a candidate for the intragastric balloon 44 as much water 48 as possible over a 10 minute period of time.

STEP 2: Monitoring volume of the water 48 ingested.

STEP 3: Advising by the individual patient 46 to a physician 50 or person 52 administering the method 40 when the individual patient 46 feels uncomfortably bloated or alternatively, if the individual patient 46 vomits, the volume of the water 48 ingested will be determined.

STEP 4: Selecting for the individual patient 46 the intragastric balloon 44 that is a fraction of the volume leading to uncomfortable symptoms, with the volume of the intragastric balloon 44 being 75% of the ingested volume of water 48.

STEP 5: Monitoring the individual patient 46 with specialized equipment 54 during ingestion, as with, but not limited to, an electrogastrograph 56, an upper endoscope 58, or a barostat balloon 60.

STEP 6: Challenging over time, the individual patient 46 with the intragastric balloon 44 with another load of water 48 as in STEP 1 above to see if the individual patient 46 can tolerate a larger intragastric balloon 44 because it is anticipated that a larger intragastric balloon 44 might be expected to have a greater therapeutic effect in the management of obesity and satiety symptoms.

In the above embodiment, the water 48 is specified as material 62 ingested. The water 48 is only mentioned as a preferred example. The material 62 ingested may be a water solution suspension 64, or other non-aqueous based material 66. Temperature 68 is implied as room temperature 70, but may be some other temperature 72. Time 74 is specified as 10 minutes, but may be some other interval of time 76.

B. An Intragastric Balloon for Inflating without Installation of a Pressurized Gas or Liquid As shown in FIG. 3, which is a diagrammatic side elevational view in partial section of a balloon of an embodiment of the present invention fully expanded within a stomach, an intragastric balloon 78 comprises a plurality of struts 80. The plurality of struts 80 form a skeleton 82 of the intragastric balloon 78, run longitudinally, are parallel to protrusions 84 and channels 86 of the intragastric balloon 78, are fabricated out of a metal or a composite with a memory for its shape 90, such as nitinol, and are shaped so that when released, they expand to fill out volume 92 of the intragastric balloon 78, with this shape being the shape that would otherwise be created if the intragastric balloon 78 was inflated with air, water, or both.

The intragastric balloon 78 further comprises a valve 100 or opening 102 to allow air and gastric fluid into the intragastric balloon 78 as the intragastric balloon 78 is expanded in the gastric environment 106.

In one embodiment, the plurality of struts 80 have holes 108 or other fastening points 110 midway. These fastening points 110 are connected by internal wires 112 to a central longitudinal strut 114 of the plurality of struts 80 running straight and longitudinally through the length of the balloon 78. One end 118 or portion 120 of this central longitudinal strut 114 of the plurality of struts 80 is accessible by an endoscopic device 122.

In another embodiment, with the balloon 78 held steadily in position with an endoscopic forceps 124 or an Ewald tube, an instrument can grasp the end 118 of the central longitudinal strut 114 of the plurality of struts 80 and pull it. This would collapse the balloon 78, allowing it to be removed from the stomach 126 in its collapsed state.

In another embodiment, there is a shelf or ledge that allows the balloon 78 to be stabilized against a standard 36 French Ewald tube to facilitate traction on the central longitudinal strut 114 of the plurality of struts 80.

In another embodiment, there would be a grasping point 132 for the endoscopic forceps 124 to grasp and stabilize the balloon 78 for removal from the stomach 126.

In another embodiment, the plurality of struts 80 obtain their curved shapes by being configured of two parallel layers of metals 134 with different coefficients of thermal expansion. In this embodiment, the balloon 78 is chilled with ice before its deployment though the esophagus 136 into the stomach 126. At body temperature, the plurality of struts 80 expand to their designed shapes. On removal, the stomach 126 is lavaged with ice water to allow the plurality of struts 80 of the balloon 78 to shrink.

In another embodiment, the central longitudinal strut 114 of the plurality of struts 80 is a spring 138. The spring 138 is stretched when the balloon 78 is collapsed and ready to deploy in the stomach 126. When released in the stomach 126, the spring 138 retracts to its non-stretched length, expanding the balloon 78. The spring 138 gives the balloon 78 more resilience, almost like a shock absorber, in the gastric environment 106.

Figure 4:
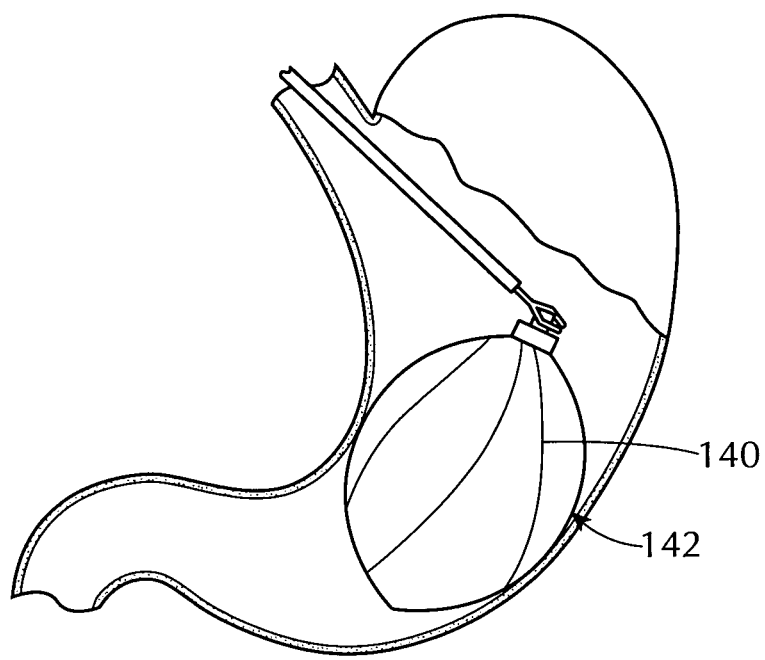
FIG. 4 is a diagrammatic side elevational view in partial section of a balloon of another embodiment of the present invention fully expanded within a stomach.

C. An Intragastric Balloon for Minimizing Trauma of the Intragastric Balloon on the Gastric Mucosa As shown in FIG. 4, which is a diagrammatic side elevational view in partial section of a balloon of another embodiment of the present invention fully expanded within a stomach, the plurality of protrusions 140 of the balloon 142 run diagonally rather than longitudinally.

Figure 5:
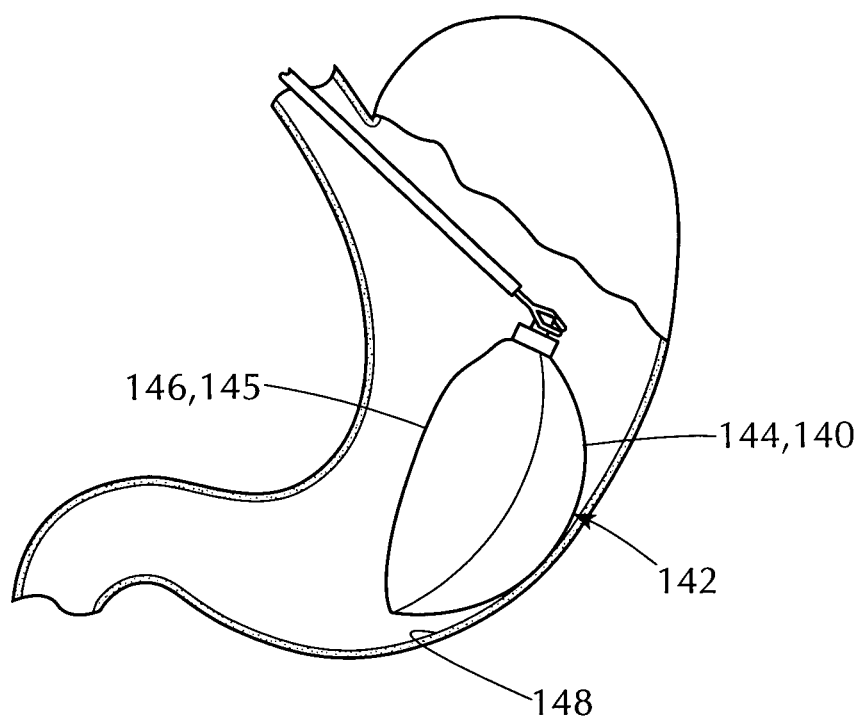
FIG. 5 is a diagrammatic side elevational view in partial section of a balloon of another embodiment of the present invention fully expanded within a stomach.

As shown in FIG. 5, which is a diagrammatic side elevational view in partial section of a balloon of another embodiment of the present invention fully expanded within a stomach, in another embodiment, one 144 of the plurality of protrusions 140 is made more prominent. On an opposite side 145 of the balloon 142, another one 146 of the plurality of protrusions 140 is made less prominent. When a gastric peristaltic wave passes over the balloon 142, more pressure is placed on the one 144 of the plurality of protrusions 140 that is more prominent and less on the one 146 of the plurality of protrusions 140 that is less prominent. As the balloon 142 impacts the antral wall 148 distally, there is a tendency for the balloon 142 to rotate along its long axis, which is repeated with every peristaltic wave, so that different points are presented to the gastric mucosa.

Figure 6:
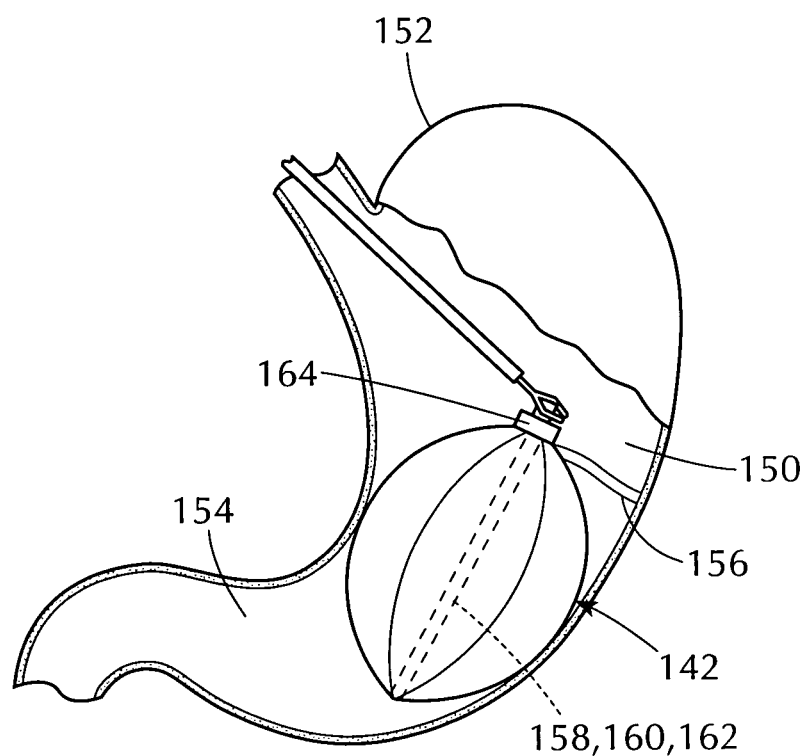
FIG. 6 is a diagrammatic side elevational view in partial section of a balloon of another embodiment of the present invention fully expanded within a stomach.

As shown in FIG. 6, which is a diagrammatic side elevational view in partial section of a balloon of another embodiment of the present invention fully expanded within a stomach, in another embodiment, the balloon 142 is tethered by at least one tether 156 to a proximal portion 150 of the stomach 152 to prevent forward migration of the balloon 142 to impact in the distal antrum 154. With the one tether 156 attached to long axis 158 of the central longitudinal strut 160 of the plurality of struts 162, the balloon 142 is able to rotate freely with a ball and socket assembly 164. With the at least one tether 156 attached to the balloon 142, the balloon 142 twists on the at least one tether 156 and then is forced to turn backwards due to tension on the at least one tether 156. The at least one tether 156 is attached to the balloon 142 and the proximal portion 150 of the stomach 152 to maximize stimulation of this area to maximize effects of ghrelin or other digestive hormones associated with the stomach 152.

Figure 7:
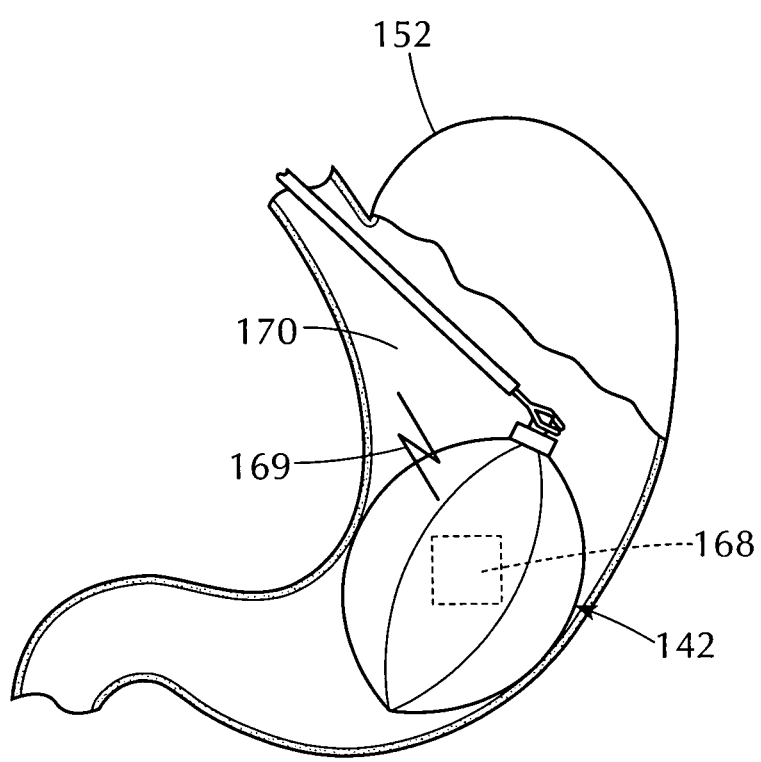
FIG. 7 is a diagrammatic side elevational view in partial section of a balloon of another embodiment of the present invention fully expanded within a stomach.

As shown in FIG. 7, which is a diagrammatic side elevational view in partial section of a balloon of another embodiment of the present invention fully expanded within a stomach, in another embodiment, an electrical device 168 is incorporated into the balloon 142 to provide electrical signals 169 to the antrum 170 of the stomach 152 to maximize stimulating effects of ghrelin and other digestive hormones.

Figure 8:
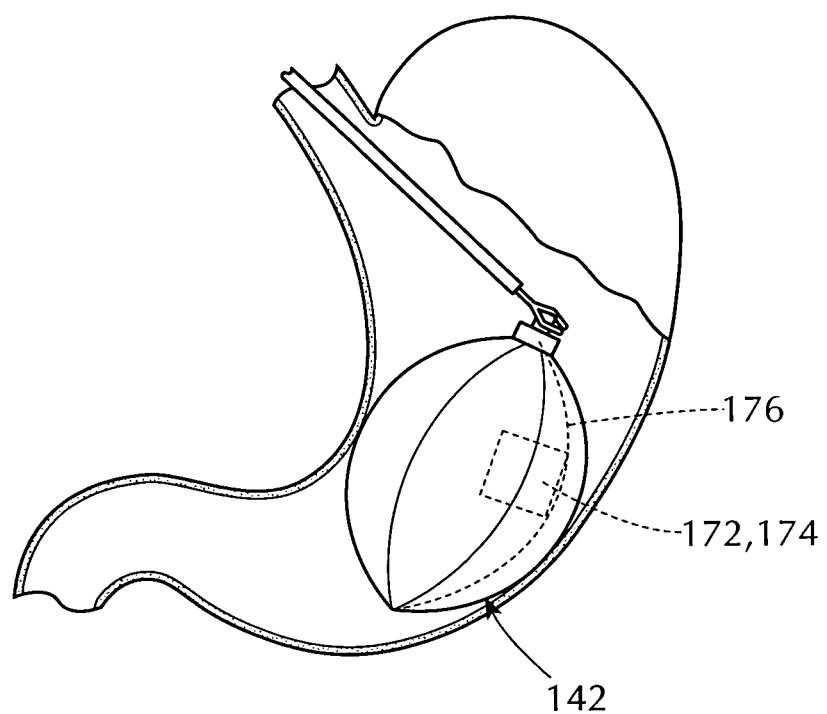
FIG. 8 is a diagrammatic side elevational view in partial section of a balloon of another embodiment of the present invention fully expanded within a stomach.

As shown in FIG. 8, which is a diagrammatic side elevational view in partial section of a balloon of another embodiment of the present invention fully expanded within a stomach, in another embodiment, a counterweight 172 is built into the balloon 142 to accentuate eccentricity of the balloon 142 and allow it to spin. This can be a fixed counterweight 174 or attached to the plurality of struts 176 of the balloon 142.

D. An Intragastric Balloon for Administering Therapeutic Medications

Figure 9:
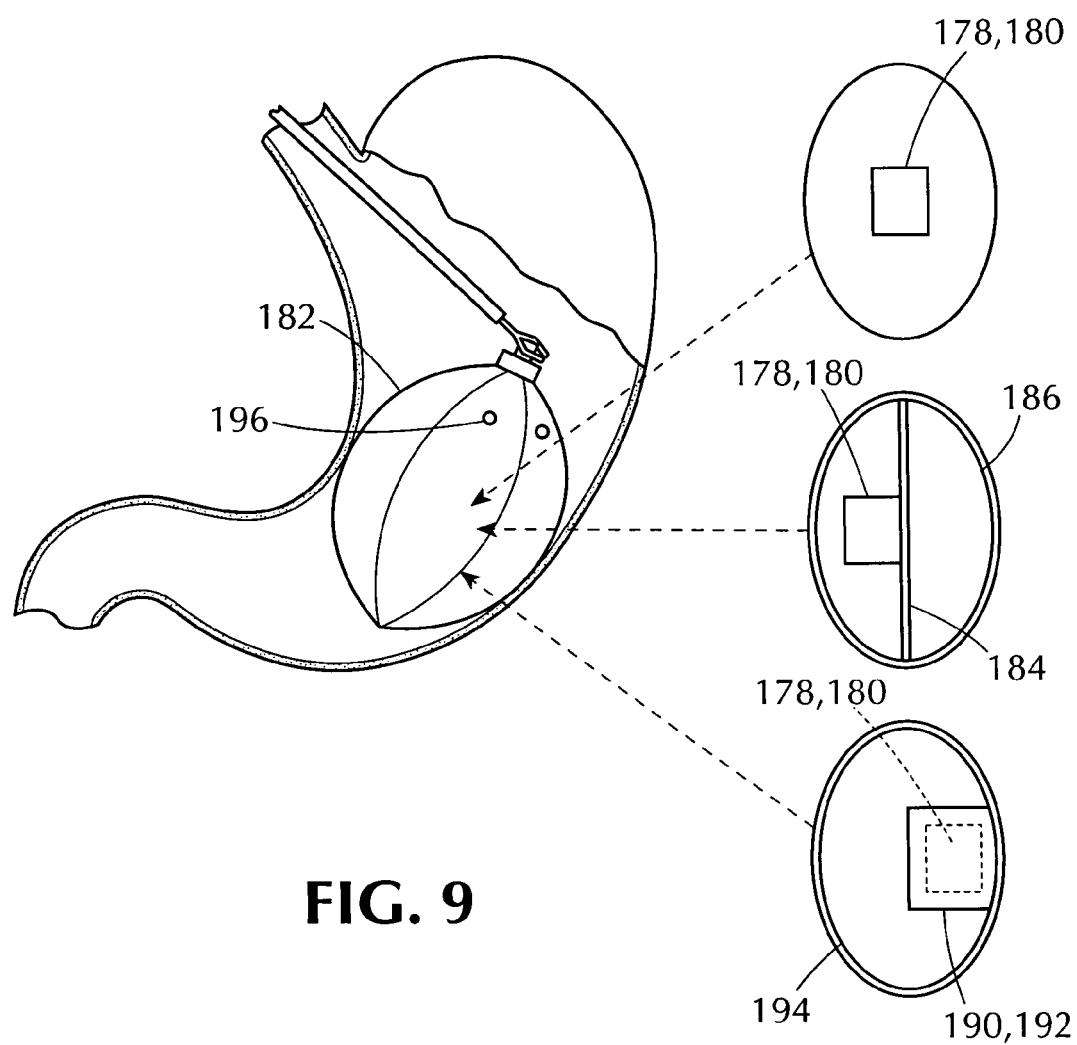
FIG. 9 is a diagrammatic side elevational view in partial section of a balloon of another embodiment of the present invention fully expanded within a stomach.

As shown in FIG. 9, which is a diagrammatic side elevational view in partial section of a balloon of another embodiment of the present invention fully expanded within a stomach, a therapeutic medication 178 is placed in a matrix 180 that is slowly dissolving and inert. This matrix 180 is deployed loosely in the balloon 182 or fabricated to attach to one 184 of the struts 186 of the balloon 182 or inside a pocket 190 or attachment 192 in the wall 194 of the balloon 182.

The balloon 182 is fabricated with holes 196 to freely allow the gastric contents 198 to enter the balloon 182. The matrix 180 slowly dissolves, thereby releasing the therapeutic medication 178.

E. A Method for Using an Enterocutaneous Fistula to Inspect an Intragastric Balloon without Sedation and Endoscopic Complications Associated with Upper Endoscopy As shown in FIGS. 10A-10B, which are a flowchart of the method of another embodiment of the present invention for using an enterocutaneous fistula to inspect an intragastric balloon without sedation and endoscopic complications associated with an upper endoscopy, the method of the embodiment of the present invention is shown generally at 200 for using an enterocutaneous fistula 202 to inspect an intragastric balloon 204 without sedation and endoscopic complications associated with an upper endoscopy, and comprises the steps of:

STEP 1: Placing a percutaneous gastrostomy 206 in a usual manner.

STEP 2: Allowing the percutaneous gastrostomy 206 to heal.

STEP 3: Dilating the tract 208 to allow passage of an upper endoscope 210 directly into the stomach 212.

STEP 4: Evaluating the balloon 204 and the gastric mucosa 214.

F. A Method for Restricting Expansion of the Stomach for an Individual Patient As shown in FIGS. 11A-11E, which are a flowchart of the method of another embodiments of the present invention for restricting expansion of the stomach for an individual patient, the method of the embodiment of the present invention is shown generally at 218 for decreasing ability of the stomach 220 of an individual patient 222 to distend or expand after a meal 224 increasing satiety and helping the individual patient 222 to comply with a weight loss diet 226, and comprises the steps of:

STEP 1: Attaching a balloon 228 or other space occupying device 230 or pillow 232 to a band 234 that is of cloth, is 3 inches wide, is one of resistant to stretching and elastic, has a width 236 that is dependent upon the weight 238 of the individual patient 222 and anatomy 240 of the individual patient 222, and has a portion 242 thereof widened compared to the rest of the band 234 to accommodate one of a pressure pack 244 and a balloon 246.

STEP 2: Utilizing an adhesive 248 on at least one of the skin 250 of the individual patient 222 and the band 234 to prevent the band 234 from migrating while being worn by the individual patient 222.

STEP 3: Utilizing one of a standard tee shirt 252 and other shirt 254 having a separate tube 256 within or outside of it allowing the band 234 and/or the space-occupying device 230 to be enclosed so that it will be covered or disguised by the separate tube 256.

STEP 4: Utilizing roentgenography 258 or fluoroscopy 260 to locate the stomach 220 of the individual patient 222 to facilitate proper placement of the band 234 and the space-occupying device 230.

STEP 5: Wrapping the band 234 around the stomach 220 of the individual patient 222 in one of an area caudal to the xiphoid process 262 of the sternum 264 and cranial to the lower edge 266 of the rib cage 268 of the individual patient 222 and along the circumference 270 of the portion 272 of the stomach 220 of the individual patient 222 with the greatest diameter 274 and in a repeating FIG. 8 so that different areas of the skin 250 of the individual patient 222 are touched by the band 234 allowing adjacent areas to recover from tension of the band 234.

STEP 6: Closing/attaching the band 234 with one of buttons 276 and hook and loop fasteners (VELCRO®) 278.

STEP 7: Attaching a pulley device 280 to one end 282 of the band 234 for use in tightening the band 234.

STEP 8: Applying pressure to the left upper quadrant portion 284 of the stomach 220 of the individual patient 222 by use of one of the balloon 228, the other space-occupying device 230, and the pillow 232.

STEP 9: Utilizing one of pulse oximetry 286, blood gas measurement 288, and capnography 290 to determine if the band 234 significantly decreases respiratory status of the individual patient 222.

STEP 10: Measuring tension 292 of the band 234 and tension applied to the skin 250 of the individual patient 222 to ascertain likelihood of causing damage or ulceration to the skin 250 of the individual patient 222.

In another embodiment, outside appearance of the shirt 254 appears normal to an observer, with the band 234 held in place by the cloth tube 256. The cloth tube 256 is of such a volume that when the band 234 is activated, there would be sufficient space to allow the shirt 254 to hang freely.

In another embodiment, the band 234 is incorporated into the tee shirt 252 in such a way that it is obvious to a casual observer creating an obvious constriction.

In another embodiment, a device with the appearance of standard suspenders is attached to an adjustable belt around the waist of the individual patient 222 to hold the band 234 in a proper position as with one of hook and loop fasteners (Velcro), buttons, and snap devices.

G. The Conclusions

It will be understood that each of the elements described above or two or more together may also find a useful application in other types of constructions differing from the types described above.

While the embodiments of the present invention have been illustrated and described as embodied in a multi-method and multi-apparatus for treating obesity, however, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

Without further analysis the foregoing will so fully reveal the gist of the embodiments of the present invention that others can by applying current knowledge readily adapt them for various applications without omitting features that from the standpoint of prior art fairly constitute characteristics of the generic or specific aspects of the embodiments of the present invention.

The invention claimed is:

1. An apparatus for treating obesity and being of the type having a balloon that is flexible-walled, imperforate, air-inflatable, and includes a volume, and is insertable and inflatable within the stomach of a human or animal to deter ingestion of food by occupying a substantial portion of the volume of the stomach, and a plurality of wall portions forming protrusions that are smooth-surfaced and convex outward when inflated and are distributed around the balloon and cooperatively define a plurality of channels that are outwardly open for passage of fluent material between the outer surface of the balloon and the wall of the stomach, and are shaped and disposed to permit engagement of the wall of the stomach by the balloon only at spaced localities so as to maintain a substantial portion of the wall of the stomach away from contact with the balloon for minimizing complications due to mechanical trauma of the balloon against the wall of the stomach, the apparatus comprising:
a plurality of struts forming a skeleton of the balloon, running longitudinally, and being parallel to the protrusions and the channels of the balloon for inflating the balloon without installation of a pressurized gas or liquid by having a shape that when released expands to fill out the volume of the balloon, the plurality of struts comprising holes midway therealong, the holes connected by internal wires to a central strut running straight and longitudinally through the length of the balloon.

2. The apparatus of claim 1, wherein the shape of the plurality of struts comprises a shape that would otherwise be created if the balloon was inflated with a medium selected from the group consisting of at least one of air and water.

3. The apparatus of claim 1, wherein the plurality of struts are fabricated out of one of a memory metal and a memory composite.

4. The apparatus of claim 3, wherein the memory metal of the plurality of struts comprises nitinol.

5. The apparatus of claim 1, wherein the balloon comprises at least one of a valve and an opening adapted to allow air and gastric fluid into the balloon as the balloon is expanded in the gastric environment.

6. The apparatus of claim 1, wherein
at least one of one end and a portion of the central longitudinal strut is accessible by an endoscopic device.

7. The apparatus of claim 6, further comprising:
at least one of a shelf and a ledge allowing the balloon to be stabilized against a standard 36 French Ewald tube to facilitate traction on the central longitudinal strut.

8. The apparatus of claim 1, wherein the plurality of struts comprise two parallel layers of metals with different coefficients of thermal expansion for obtaining curved shapes.

9. The apparatus of claim 1, further comprising:
a spring;
wherein the spring is stretched when the balloon is collapsed and ready to deploy in the stomach, and when released in the stomach, the spring retracts to its non-stretched length expanding the balloon; and
wherein the spring gives the balloon more resilience in the gastric environment.

10. The apparatus of claim 1, wherein the protrusions of the balloon run diagonally.

11. The improvement of claim 1, wherein at least one of the protrusions is made more prominent, and on an opposite side of the balloon another one of the protrusions is made less prominent thereby allowing, when a gastric peristaltic wave passes over the balloon, more pressure to be placed on the one of the protrusions that is more prominent and less on the another one of the protrusions that is less prominent thereby allowing, as the balloon impacts the antral wall distally, a tendency for the balloon to rotate along its long axis, which is repeated every peristaltic wave so as to allow different points to be presented to the gastric mucosa.

12. The apparatus of claim 6, wherein
the balloon is tethered by at least one tether to a proximal portion of the stomach to prevent forward migration of the balloon to impact in the distal antrum;
wherein one tether is attached to a long axis of the central strut so as to allow the balloon to rotate with a ball and socket assembly;
wherein the at least one tether is attached to the balloon and adapted to allow the balloon to twist on the at least one tether and then be forced to turn backwards due to tension on the at least one tether; and
wherein the at least one tether is attached to the balloon and the proximal portion of the stomach to maximize stimulation of this area to maximize effects of ghrelin or other digestive hormones associated with the stomach.

13. The apparatus of claim 1, further comprising:
an electrical device incorporated into the balloon, the electrical device adapted to provide electrical signals to the antrum of the stomach to maximize stimulating effects of ghrelin and other digestive hormones.

14. The apparatus of claim 1, further comprising:
a counterweight built into the balloon, the counterweight adapted to accentuate eccentricity of the balloon and allow it to spin.

15. The apparatus of claim 14, wherein the counterweight comprises at least one of a fixed counterweight and a counterweight that is attached to the plurality of struts of the balloon.

16. The apparatus of claim 1, further comprising:
a therapeutic medication placed in a matrix that slowly dissolves and is inert; and
wherein the matrix is one of deployed loosely in the balloon, fabricated to attach to one of the struts of the balloon, inside a pocket, and an attachment in the wall of the balloon.

17. The improvement of claim 16, wherein the balloon is fabricated with holes adapted to freely allow the gastric contents to enter the balloon, with the matrix slowly dissolving thereby releasing the therapeutic medication.

* * * * *